(12) United States Patent
Kim et al.

(10) Patent No.: US 9,273,016 B2
(45) Date of Patent: Mar. 1, 2016

(54) PROCESS FOR PREPARING DISUBSTITUTED UREA AND CARBAMATE COMPOUNDS FROM AMINES, CARBON DIOXIDE, AND EPOXIDES

(71) Applicant: Korea Institute of Industrial Technology, Chungcheongnam-do (KR)

(72) Inventors: Yong Jin Kim, Chungcheongnam-do (KR); Vivek Mishra, Chungcheongnam-do (KR); Guang Meang Son, Daejeon (KR); Jin Ku Cho, Gyeonggi-do (KR); Baek Jin Kim, Chungcheongnam-do (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 39 days.

(21) Appl. No.: 14/136,629

(22) Filed: Dec. 20, 2013

(65) Prior Publication Data

US 2015/0133676 A1    May 14, 2015

(30) Foreign Application Priority Data

Nov. 14, 2013    (KR) .......................... 10-2013-0138142

(51) Int. Cl.
| | | |
|---|---|---|
| *C07D 263/04* | (2006.01) | |
| *C07D 263/22* | (2006.01) | |
| *C07C 269/04* | (2006.01) | |
| *C07C 273/18* | (2006.01) | |

(52) U.S. Cl.
CPC ............ *C07D 263/22* (2013.01); *C07C 269/04* (2013.01); *C07C 273/1836* (2013.01); *C07C 2101/14* (2013.01)

(58) Field of Classification Search
CPC .................................................... C07D 263/04
See application file for complete search history.

(56) References Cited

U.S. PATENT DOCUMENTS

| | | | |
|---|---|---|---|
| 2,877,268 A | 3/1959 | Applegath et al. | |
| 4,052,454 A | 10/1977 | Zajacek et al. | |
| 4,268,684 A | 5/1981 | Gurgiolo | |
| 4,484,994 A | 11/1984 | Jacobs, III et al. | |
| 4,550,188 A | 10/1985 | Frulla et al. | |
| 4,631,320 A | 12/1986 | Parekh et al. | |
| 5,180,785 A | 1/1993 | Uryu et al. | |
| 6,165,338 A | 12/2000 | December et al. | |

FOREIGN PATENT DOCUMENTS

| | | |
|---|---|---|
| EP | 0319111 A2 | 6/1989 |
| JP | 62059253 | 3/1987 |
| JP | 10287625 A | 10/1998 |
| JP | 2012111711 A | 6/2012 |
| KR | 1019850006699 | 10/1985 |
| KR | 1019910009114 | 5/1991 |
| KR | 1019990060692 B1 | 7/1999 |

OTHER PUBLICATIONS

Chaturvedi, 2012, Tetrahedron, vol. 68, p. 15-45.*
Gu, 2012, Green Chem, vol. 14, p. 2091-2128.*
Yoshida, 1979, J. Chem. Soc., Perkin Trans, vol. 1, p. 3146-3150.*
Franz et al., "A New Synthesis of Ureas. III. The Reaction of Aromatic Amines with Carbon Monoxide and Sulfur," *J. Org. Chem*, 26:3309-3312 (1961).
Kondo et al., "A New Synthesis of Carbamates. The Reaction of Carbon Monoxide with Amine and Alcohol in the Co-presence of Selenium and Triethylamine," Chemistry Letters, pp. 373-374 (1972).
Patil et al., "Carbon Dioxide: A Renewable Feedstock for the Synthesis of Fine and Bulk Chemicals," *Front. Chem. Eng. China*, 4(2):213-235 (2010).
Notice of Allowance for Korean Patent Application No. 10-2013-0138142, dated Dec. 29, 2015.

* cited by examiner

*Primary Examiner* — Michael Barker
*Assistant Examiner* — Karen Cheng
(74) *Attorney, Agent, or Firm* — Marshall, Gerstein & Borun LLP

(57) ABSTRACT

The present disclosure relates to a method for preparing a disubstituted urea and carbamate compounds simultaneously through a one-pot reaction of an amine, carbon dioxide and an alkylene oxide compound in the presence of an ionic liquid-based complex catalyst system containing indium. In accordance with the present disclosure, a disubstituted urea and carbamate compounds can be prepared simultaneously at high yield. In addition, the ionic liquid-based catalyst containing indium according to the present disclosure is economical because it can be reused several times.

9 Claims, No Drawings

PROCESS FOR PREPARING DISUBSTITUTED UREA AND CARBAMATE COMPOUNDS FROM AMINES, CARBON DIOXIDE, AND EPOXIDES

CROSS-REFERENCE TO RELATED APPLICATIONS

This application claims priority under 35 U.S.C. §119 to Korean Patent Application No. 10-2013-0138142, filed on Nov. 14, 2013, in the Korean Intellectual Property Office, the disclosure of which is incorporated herein by reference in its entirety.

TECHNICAL FIELD

The present disclosure relates to a method for preparing a disubstituted urea and carbamate compounds by reacting an amine, carbon dioxide and an alkylene oxide compound in the presence of an ionic liquid-based catalyst system, more particularly to a method for preparing a disubstituted urea and carbamate compounds simultaneously through a one-pot reaction of an amine, carbon dioxide and an alkylene oxide compound in the presence of an ionic liquid-based complex catalyst system containing indium.

BACKGROUND

Disubstituted ureas are usefully used as starting materials or intermediates of agrichemicals, herbicides, insecticides and carbamates and various methods for their preparation are being studied.

The existing method of preparing urea by reacting an amine with phosgene is disadvantageous in that the highly toxic and corrosive phosgene is used and a large amount of the pollutant HCl is produced as byproduct. Accordingly, methods for preparing urea without using the harmful phosgene have been studied in the US, Japan and Europe.

U.S. Pat. No. 2,877,268 discloses a method for preparing urea by reacting an amine with carbonyl sulfide (COS) in the absence of a catalyst, and the literature "*J. Org. Chem.* (R. A. Franz, 26, p. 3309, 1961)" discloses a method for preparing urea by reacting an amine with carbon monoxide (CO) and sulfur (S) using a tertiary amine as a catalyst. However, these methods are problematic in that byproducts difficult to handle such as $H_2S$ are produced because sulfur is used.

Japanese Patent Publication No. S62-59253 discloses a method for preparing urea from a nitro compound using a catalyst such as rhodium, ruthenium, etc. Although this method allows preparation of urea with relatively high conversion rate and selectivity, the expensive noble metal catalyst may be easily decomposed because of high reaction temperature and pressure.

European Patent No. 0 319 111 discloses a method for preparing urea from a mixture of an amine and nitrobenzene using a noble metal catalyst palladium with a salt of copper, iron, manganese, vanadium, chromium, etc. added to maintain the activity of the palladium catalyst. As described in Example 1 of the EP 0 319 111, this method is problematic in that the maximum yield of urea is low as 73% (turnover frequency, i.e., the number of moles of urea produced per unit time, per a mole of catalyst <4) when reacted for 20 hours under the condition of 140° C. and 50 atm.

A method for synthesizing aliphatic urea by carbonylation of an amine in the presence of a selenium catalyst is described in "*Chemistry Letters* (Koyoshi Kondo, p. 373, 1972)". This method is problematic in that a large amount of the catalyst is spent since the selenium is used in an equimolar amount with respect to the starting material amine and that the reaction hardly proceeds if an aromatic amine is used as the starting material.

U.S. Pat. No. 4,052,454 discloses a method for synthesizing urea by reacting a nitro compound with water and carbon monoxide in the presence of a selenium metal catalyst. This method is economically unfavorable since, as described in Example 1 of the U.S. Pat. No. 4,052,454, nitrobenzene conversion rate and urea yield are only 66.3% and 33.8% (turnover frequency, i.e., the number of moles of urea produced per unit time, per a mole of catalyst <2) when reacted for 1 hour under the condition of 150° C. and 53 atm, with a molar ratio of the catalyst to the starting material nitrobenzene of about ⅛.

As described above, the existing methods for preparing substituted urea are inappropriate for preparation of the substituted urea in industrial scale because of byproduct formation, reaction condition with high temperature and pressure, and low yield, and are problematic in that it is difficult to prepare urea in high yield when a less reactive aromatic amine is used as a starting material in spite of the reaction condition with high temperature and pressure. And, the method for preparing urea using selenium as a catalyst also has a problem because of the characteristic unpleasant odor of selenium after the reaction under the condition with high temperature and pressure.

Hydroxyalkyl carbamates are synthetic intermediate useful in various fields, including drug synthesis and agrichemical production, and as precursors of polyurethane.

As an existing method for preparing a hydroxyalkyl carbamate, Korean Patent No. 10-0050365 discloses preparation of 2-hydroxypropyl carbamate by reacting propylene carbonate with a primary or secondary aliphatic amine.

Also, U.S. Pat. No. 4,268,684 (Arthur E. Gurgiolo) discloses a method for preparing an aromatic carbamate by reacting an aromatic amine, e.g., aniline, with dimethyl carbonate, and U.S. Pat. No. 4,550,188 discloses a catalyst for reacting an aromatic amine with an organic carbonate, including a mercury salt and iodine. However, there are problems of the toxicity of mercury and low performance of the catalyst. Also, the aromatic polyurethane derived from the aromatic carbamate synthesized from the aromatic amine has unsatisfactory physical and chemical properties as compared to aliphatic polyurethane due to yellowing.

Meanwhile, Korean Patent Publication No. 1991-0009114 relates to a novel hydroxyalkyl carbamate having one or more secondary amine groups in the molecule and a method for preparing same, and describes preparation of a hydroxyalkyl carbamate from a polyfunctional amine having at least one primary amine group and at least one hindered secondary amine group, wherein the primary amine group(s) react(s) selectively with a cyclic carbonate and the secondary amine group(s) remain(s) unreacted.

Korean Patent No. 10-0576404 relates to a β-hydroxyalkyl carbamate-modified resin for pigment dispersion and a cationic electrodeposition paint composition containing same, and describes preparation of a β-hydroxyalkyl carbamate from reaction of a cyclic carbonate with a polyepoxide-amine resin.

U.S. Pat. No. 6,165,338 relates to a cathodic electrodeposition coating composition and describes preparation of a hydroxyalkyl carbamate from reaction of a primary or secondary amine or diamine with a cyclic carbonate such as ethylene carbonate.

SUMMARY

The present disclosure is directed to providing a method for preparing a disubstituted urea and carbamate compounds simultaneously with high yield from an amine as a starting material, more particularly a method for preparing a disubstituted urea and carbamate compounds simultaneously through a one-pot reaction of an amine, carbon dioxide and an alkylene oxide compound in the presence of an ionic liquid-based complex catalyst system containing indium.

In one general aspect, there is provided a method for preparing a disubstituted urea represented by Chemical Formula 1 and carbamate compounds represented by Chemical Formula 2 and Chemical Formula 3 simultaneously by reacting an amine, carbon dioxide and an alkylene oxide compound in the presence of an ionic liquid-based catalyst system containing indium:

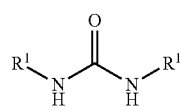

[Chemical Formula 1]

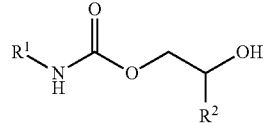

[Chemical Formula 2]

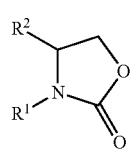

[Chemical Formula 3]

wherein $R^1$ is a $C_2$-$C_{10}$ aliphatic alkyl group, a $C_4$-$C_{10}$ alicyclic alkyl group or a $C_5$-$C_6$ aryl group, wherein the terminal of the alkyl group or aryl group may be either substituted with a hydroxyl group, an acyl group, a carboxyl group, a halogen atom or an —$NH_2$ group or unsubstituted; and $R^2$ is a $C_1$-$C_{10}$ aliphatic alkyl group, a $C_4$-$C_{10}$ alicyclic alkyl group, a $C_5$-$C_6$ aryl group, a hydrogen atom, or a halogen atom.

The ionic liquid-based catalyst system containing indium is a complex catalyst system represented by Chemical Formula 6 consisting of a main catalyst represented by Chemical Formula 4 and an alkali metal halide represented by Chemical Formula 5 as a promoter:

[Q][InX$_{(4-n)}$Y$_n$]   [Chemical Formula 4]

MZ   [Chemical Formula 5]

[Q][InX$_{(4-n)}$Y$_n$]-MZ   [Chemical Formula 6]

wherein

[Q] stands for a cation of an ionic liquid, [InX$_{(4-n)}$Y$_n$] stands for an anion of the ionic liquid and MZ stands for an alkali metal halide, wherein Q is imidazolium, phosphonium, ammonium or pyridinium, X is Cl, Br or I, Y is Cl or Br, M is an alkali metal, Z is Cl, Br or I, and n is an integer from 0 to 3.

The cation of the ionic liquid may be selected from a group consisting of 1-butyl-3-methylimidazolium (Bmim), tetra-n-butylphosphonium (TBP), tetra-n-butylammonium (TBA), tetra-n-butylpyridinium ($C_4$Py) and choline (Chol).

The anion of the ionic liquid may be selected from a group consisting of InCl$_4$, InCl$_3$Br, InCl$_3$I, InBr$_3$Cl and InBr$_4$.

And, the alkali metal halide may be selected from a group consisting of NaI, NaBr, NaCl, KI, KBr, KCl, RbI, RbBr, RbCl, LiI, LiBr, LiCl, CsI, CsBr and CsCl.

Specifically, the compound represented by Chemical Formula 4 may include but is not limited to [Bmim][InCl$_4$], [Bmim][InCl$_3$Br], [Bmim][InCl$_3$I], [Bmim][InBr$_3$Cl], [Bmim][InBr$_4$], [Bmim][InI$_4$], [TBP][InCl$_4$], [TBP][InBr$_4$], [TBP][InI$_4$], [C$_4$Py][InCl$_4$], [C$_4$Py][InBr$_4$], [C$_4$Py][InI$_4$], [Chol][InCl$_4$], [Chol][InBr$_4$] and [Chol][InI$_4$].

The main catalyst may be used in an amount of 1/5000-1/50 equivalent, specifically 1/2500-1/100 equivalent, based on the moles of the amine.

The main catalyst and the promoter may be added at an equivalence ratio of 1:1-1:5.

The alkylene oxide may be used in an amount of 0.5-2 equivalents based on the moles of the amine.

The amine may be a compound represented by Chemical Formula 7 and the alkylene oxide may be a compound represented by Chemical Formula 8 or Chemical Formula 9:

$R^1$—$NH_2$   [Chemical Formula 7]

wherein $R^1$ is a $C_2$-$C_{10}$ aliphatic alkyl group, a $C_4$-$C_{10}$ alicyclic alkyl group or a $C_5$-$C_6$ aryl group, wherein the terminal of the alkyl group or aryl group may be either substituted with a hydroxyl group, an acyl group, a carboxyl group, a halogen atom or an —$NH_2$ group or unsubstituted;

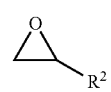

[Chemical Formula 8]

wherein $R^2$ is a $C_1$-$C_{10}$ aliphatic alkyl group, a $C_4$-$C_{10}$ alicyclic alkyl group, a $C_5$-$C_6$ aryl group, a hydrogen atom, or a halogen atom;

[Chemical Formula 9]

wherein n is an integer from 1 to 5.

The amine may be selected from a group consisting of methylamine, ethylamine, isopropylamine, butylamine, isobutylamine, hexylamine, dodecylamine, hexadecylamine, octadecylamine, benzylamine, phenylamine, cyclobutylamine, cyclohexylamine, 1,4-diaminocyclohexane, 4,4'-methylenebis(cyclohexylamine), aniline, benzylamine and phenylenediamine.

And, the alkylene oxide may be selected from a group consisting of ethylene oxide, propylene oxide, butylene oxide, cyclopentene oxide and cyclohexene oxide.

The reaction may be performed for 1-4 hours at 40-200° C. under a carbon dioxide pressure of 300-1500 psig, specifically for about 2 hours at 60-170° C. under a carbon dioxide pressure of 800-1200 psig.

The reaction may be performed either in the absence of a solvent or in the presence of a solvent.

When the reaction is performed in the presence of a solvent, it may be performed in the presence of one or more solvent selected from a group consisting of $C_1$-$C_6$ alcohol, tetrahydrofuran (THF), dimethylformamide (DMF), N-methylpyrrolidinone (NMP), dimethyl sulfoxide (DMSO), acetonitrile, toluene and dioxane.

In accordance with the present disclosure, a disubstituted urea and carbamate compounds can be prepared simultaneously at high yield by reacting an amine, carbon dioxide and an alkylene oxide compound in the presence of an ionic liquid-based catalyst system containing indium.

The disubstituted urea and carbamate compounds prepared by the present disclosure can be easily converted to isocyanates, and the isocyanates can be used as important precursor compounds that can be converted to polyurethane through reaction with polyols.

Since the method of the present disclosure allows use of an aliphatic amine as a starting material, the yellowing problem of the polyurethane derived from aromatic amines can be resolved and the physical and chemical properties of the polymer can be improved.

In addition, the ionic liquid-based catalyst containing indium according to the present disclosure is economical because it can be reused several times.

DETAILED DESCRIPTION OF EMBODIMENTS

The advantages, features and aspects of the present disclosure will become apparent from the following description of the embodiments with reference to the accompanying drawings, which is set forth hereinafter.

The reaction of the present disclosure described above is described in the following scheme.

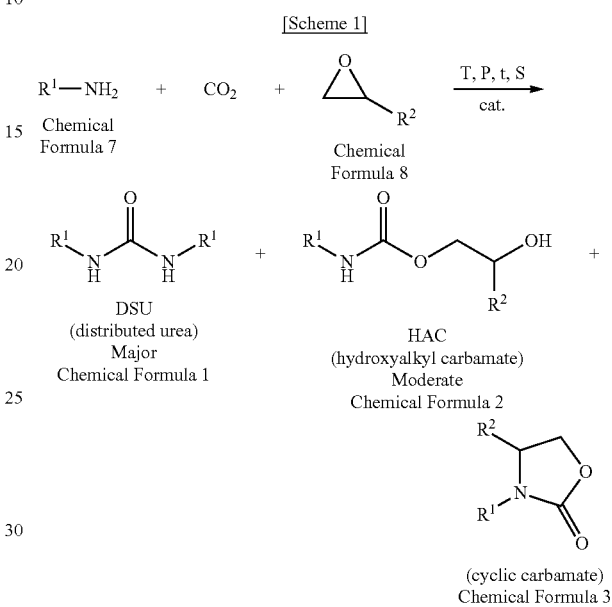

In Scheme 1, $R^1$ and $R^2$ are the same as defined in Chemical Formulas 1-3 and Chemical Formulas 7-8, cat. stands for the ionic liquid-based catalyst system of the present disclosure, T for reaction temperature, P for pressure, t for reaction time and S for organic solvent. The catalyst system and the reaction conditions are the same as described above.

Although the reaction of the present disclosure is a one-pot reaction, the reaction pathway may be represented by Scheme 2.

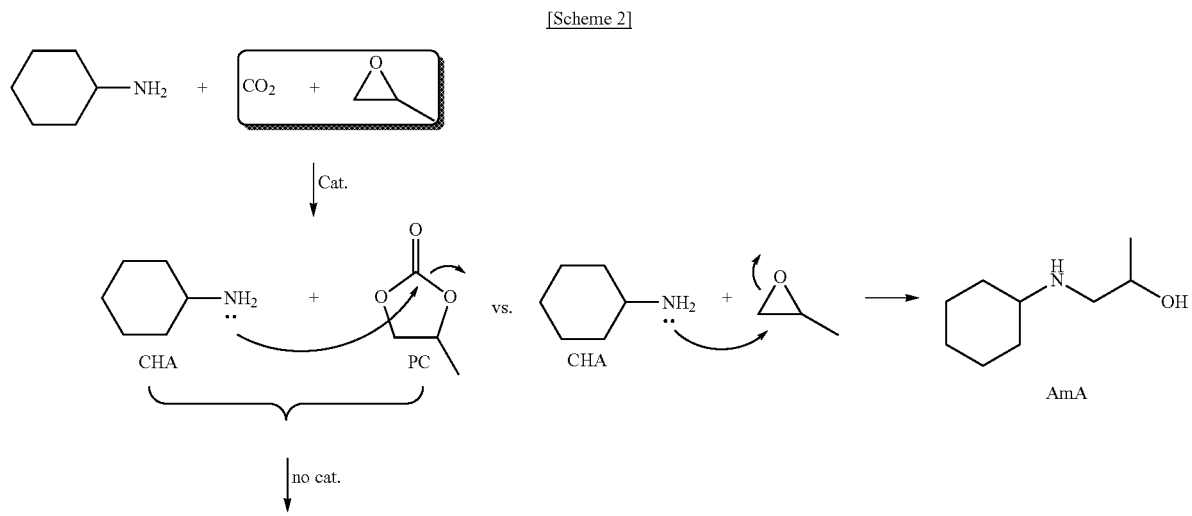

-continued

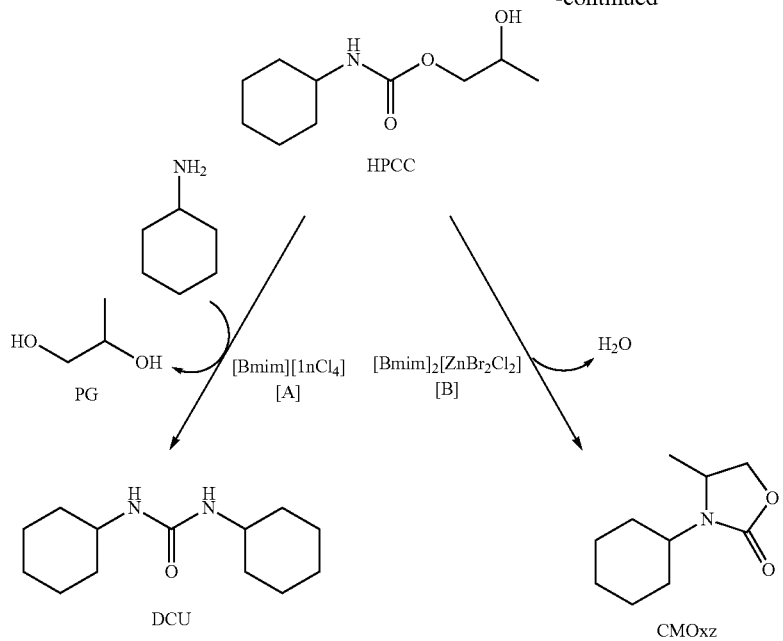

In Scheme 2, cyclohexylamine (CHA) and propylene oxide were used as starting materials and cat. stands for the ionic liquid-based catalyst system of the present disclosure.

As can be seen from Schemes 1 and 2, in the present disclosure, the starting materials, i.e., an amine (the compound represented by Chemical Formula 7 in Scheme 1, CHA in Scheme 2), carbon dioxide and an alkylene oxide (the compound represented by Chemical Formula 8 in Scheme 1, propylene oxide in Scheme 2) are reacted to produce a disubstituted urea, i.e., dicyclohexylurea (the compound represented by Chemical Formula 1 in Scheme 1, DCU in Scheme 2) and carbamate compounds, i.e., hydroxypropyl N-(cyclohexyl)carbamate (the compound represented by Chemical Formula 2 in Scheme 1, HPCC in Scheme 2) and 3-cyclohexyl-4-methyloxazolidone (the compound represented by Chemical Formula 3 in Scheme 1, CMOxz in Scheme 2).

Also, as can be seen from Scheme 2, aminoalcohol ($CyNHCH_2CHCH_3OH$, AmA) is produced as a byproduct. If byproducts such as AmA are produced in large amount, the conversion rate of CHA and the yield of DCU may decrease.

After the reaction of the present disclosure is completed, the insoluble urea may be weighed after filtration and drying to calculate its yield. The conversion rate of the amine may be calculated through gas-liquid chromatography. And, the yield of the carbamate compounds may be calculated by analyzing the residue remaining after separating the urea through gas chromatography.

In addition, the major target compound DCU can be easily separated through filtration and the catalyst can be reused by adding the starting materials to a solution in which the catalyst of the present disclosure is dissolved.

Hereinafter, the present disclosure will be described in more detail through examples. However, the following examples are for illustrative purposes only and not intended to limit the scope of this disclosure.

Example 1

Synthesis of Catalyst

[Bmim]Cl (6.2 g, 35.5 mmol) and $InCl_3$ (7.85 g, 35.5 mmol) were added to a 20-mL vial. After irradiating 600-W microwaves 3 times for 5 seconds and removing undissolved solid from the resulting liquid using a syringe filter, [Bmim][$InCl_4$] in liquid state was obtained with a yield of 98%. Also, [Bmim][$InBr_4$], [Bmim][$InI_4$], [TBP][$InCl_4$], [TBA][$InCl_4$] and [$C_4Py$][$InCl_4$] were respectively prepared by the same method. [Chol][$InCl_4$] was prepared by refluxing for 2 hours using methanol as a solvent instead of the microwave irradiation.

Example 2

Preparation of DCU and HPCC Through Reaction at High Pressure

Cyclohexylamine (CHA, also "$CyNH_2$") (4.26 g, 43 mmol), propylene oxide (PO) (43 mmol, 2.5 g), [Bmim][$InCl_4$] (0.085 g, 0.215 mmol), NaI (0.161 g, 1.075 mmol) and tetrahydrofuran (THF) (15 mL) as a solvent were added to a 100-mL high-pressure reactor equipped with a magnetic stirrer. After performing reaction for 2 hours under a $CO_2$ pressure of 1200 psig at 150° C., the reaction mixture was cooled to room temperature. After adding a predetermined amount (2 mL) of external standard, the solid product was separated. The separated solid product was washed 2-3 times with distilled water to remove cyclohexyl carbamate salt ($CyNH_3^+CyNHCOO^-$). After further washing 2-3 times with THF, the product was completely dried in a vacuum oven. After the drying, the produced dicyclohexylurea (N,N'-dicyclohexylurea, DCU) was weighed to calculate the production yield of DCU. The conversion rate (%) of CHA and the yield of DCU were calculated according to Equation 1 and Equation 2.

CHA conversion rate (%)=(Moles of reacted CHA)/(Moles of added CHA)×100    [Equation 1]

DCU yield (%)=(Moles of actually produced DCU)/(Moles of theoretically producible DCU)×100    [Equation 2]

The residue remaining after the separation of the solid product was analyzed by gas chromatography (GC) equipped with a flame ionization detector (FID) to confirm the production of hydroxypropyl N-(cyclohexyl)carbamate (HPCC), aminoalcohol ($CyNHCH_2CHCH_3OH$, AmA) and 3-cyclohexyl-4-methyloxazolidone (CMOxz). The yields of HPCC, AmA and CMOxz were calculated using the external standard. According to the GC analysis result, the CHA conversion rate was 85.9%, the DCU yield was 47.1%, the HPCC yield was 26.7%, the CMOxz yield was 9.9%, and the AmA yield was 2.1%.

Comparative Examples 1-9

Experiment was conducted under the same condition as in Example 2 while varying the catalyst and solvent in the absence of the promoter NaI. The result is shown in Table 1. As seen from Table 1, there was no significant difference in HPCC and CMOxz yields as compared to Example 2, but CHA conversion rate and DCU yield were lower and the production of reaction byproducts such as AmA was increased.

TABLE 1

| Comp. Ex. | Catalyst | Solvent | CHA conversion rate (%) | DCU yield (%) | HPCC/CMOxz yield (%) | AmA yield (%) |
|---|---|---|---|---|---|---|
| 1 | None | THF | 68.9 | 0 | 25.6/32.9 | 10.3 |
| 2 | $InCl_3$ | THF | 55.8 | 0.7 | 11.8/0.4 | 42.7 |
| 3 | [Bmim]Cl | THF | 64.6 | 2.3 | 25.6/4.3 | 31.4 |
| 4 | [Bmim][$InCl_4$] | THF | 73.1 | 23.8 | 27.4/1.7 | 15.7 |
| 5 | [Bmim]$_2$[$ZnBr_2Cl_2$] | THF | 67.5 | 3.4 | 29.8/21.4 | 9.7 |
| 6 | [Bmim][$InCl_4$] | Toluene | 75.5 | 25.8 | 15.1/6.2 | 28.5 |
| 7 | [Bmim][$InCl_4$] | Dioxane | 68.4 | 19.8 | 19.3/3.3 | 25.6 |
| 8 | [Bmim][$InCl_4$] | Methanol | 64.3 | tr. | 22.1/1.7 | 40.6 |
| 9 | [Bmim][$InCl_4$] | IPA | 72.8 | tr. | 20.6/2.4 | 49.3 |

In Table 1, tr. stands for trace amount.

Comparative Examples 10-15

Experiment was conducted under the same condition as in Example 2 while varying the promoter. The result is shown in Table 2. As seen from Table 2, when NaI was used as the promoter, there was no significant difference in HPCC and CMOxz yields, but CHA conversion rate and DCU yield were increased and the production of reaction byproducts such as AmA was suppressed. However, when other promoters were used, no ionic liquid-based catalyst was used (Comparative Example 14), or no main catalyst was used and only NaI was used (Comparative Example 15), DCU yield was very low and the production of reaction byproducts such as AmA was increased.

TABLE 2

| | Cat-Promoter | CHA conversion rate (%) | DCU yield (%) | HPCC/CMOxz yield (%) | AmA yield (%) |
|---|---|---|---|---|---|
| Comparative Example 10 | [Bmim][$InCl_4$]—$NaNO_2$ | 61.6 | 10.1 | 22.9/1.9 | 26.7 |
| Comparative Example 11 | [Bmim][$InCl_4$]—NaOH | 67.9 | 14.1 | 27.6/2.0 | 24.3 |
| Comparative Example 12 | [Bmim][$InCl_4$]—$K_2CO_3$ | 73.5 | 13.4 | 14.1/4.1 | 41.8 |
| Comparative Example 13 | [Bmim][$InCl_4$]—KOAc | 60.6 | 7.2 | 10.2/1.3 | 41.0 |
| Example 2 | [Bmim][$InCl_4$]—NaI | 85.9 | 47.1 | 26.7/9.9 | 2.1 |
| Comparative Example 14 | $InCl_3$—NaI | 78.5 | 16.2 | 17.1/19.3 | 25.9 |
| Comparative Example 15 | NaI | 73.4 | 0 | 26.2/7.5 | 39.6 |

Examples 3-16

Experiment was conducted under the same condition as in Example 2 while varying the promoter, i.e., the alkali metal halide. The result is shown in Table 3. As seen from Table 3, when LiI, NaI, KI, RbI or CsI was used as the promoter, there was no significant difference in HPCC and CMOxz yields, but CHA conversion rate and DCU yield were increased and the production of reaction byproducts such as AmA was suppressed. The DCU yield was the highest when NaI was used as the promoter.

TABLE 3

| Example | Promoter | CHA conversion rate (%) | DCU yield (%) | HPCC/CMOxz yield (%) | AmA yield (%) |
|---|---|---|---|---|---|
| 3 | LiCl | 81.3 | 21.6 | 14.8/9.0 | 35.6 |
| 4 | LiBr | 70.6 | 25.6 | 28.2/2.5 | 13.9 |
| 5 | LiI | 74.3 | 28.9 | 25.5/6.8 | 12.9 |
| 6 | NaCl | 83.1 | 18.6 | 18.5/14.8 | 30.2 |
| 7 | NaBr | 76.7 | 20.9 | 16.6/8.5 | 30.6 |
| 2 | NaI | 85.9 | 47.1 | 26.7/9.9 | 2.1 |
| 8 | KCl | 75.8 | 16.9 | 24.4/3.5 | 30.8 |
| 9 | KBr | 75.6 | 20.1 | 24.6/0.4 | 30.2 |
| 10 | KI | 85.8 | 41.2 | 25.2/4.5 | 14.4 |
| 11 | RbCl | 73.8 | 25.3 | 28.2/3.1 | 17.1 |
| 12 | RbBr | 72.3 | 30.7 | 19.5/3.4 | 18.1 |
| 13 | RbI | 75.5 | 34.3 | 28.1/9.8 | 3.0 |
| 14 | CsCl | 68.6 | 19.7 | 31.1/2.1 | 15.6 |
| 15 | CsBr | 79.2 | 22.8 | 27.9/1.4 | 26.5 |
| 16 | CsI | 76.8 | 26.1 | 22.9/12.9 | 14.5 |

Examples 17-23

Experiment was conducted under the same condition as in Example 2 while varying the ionic liquid. The result is shown in Table 4. As seen from Table 4, when [Bmim]-based ionic liquid was used, CHA conversion rate and DCU yield were increased and the production of reaction byproducts such as AmA was suppressed. In Example 23, the amount of CHA was 2 times that of Example 2. It can be seen that the result was better when the equivalence ratio of CHA to PO was 1 than when it was 2.

TABLE 4

| Example | Catalyst | CHA conversion rate (%) | DCU yield (%) | HPCC/CMOxz yield (%) | AmA yield (%) |
|---|---|---|---|---|---|
| 2 | [Bmim][InCl$_4$]—NaI | 85.9 | 47.1 | 26.7/9.9 | 2.1 |
| 17 | [Bmim][InBr$_4$]—NaI | 84.5 | 45.9 | 9.0/8.6 | 20.4 |
| 18 | [Bmim][InI$_4$]—NaI | 88.5 | 33.0 | 19.9/26.1 | 7.4 |
| 19 | [TBP][InCl$_4$]—NaI | 82.6 | 39.3 | 13.9/10.2 | 17.7 |
| 20 | [TBA][InCl$_4$]—NaI | 86.1 | 36.7 | 6.9/36.3 | 12.2 |
| 21 | [C$_4$Py][InCl$_4$]—NaI | 82.1 | 40.6 | 14.5/10.2 | 16.8 |
| 22 | [Chol][InCl$_4$]—NaI | 82.3 | 35.5 | 26.2/15.9 | 3.8 |
| 23 | [Bmim][InCl$_4$]—NaI | 43.2 | 8.3 | 21.5/0 | 6.8 |

Examples 24-27

Experiment was conducted under the same condition as in Example 2 while varying the equivalence ratio of [Bmim][InCl$_4$] to NaI from 1:1 to 1:5. The result is shown in Table 5. As seen from Table 5, when the equivalence ratio was 1:5, CHA conversion rate and DCU yield were increased and the production of reaction byproducts such as AmA was suppressed.

TABLE 5

| Example | Catalyst | CHA conversion rate (%) | DCU yield (%) | HPCC/CMOxz yield (%) | AmA yield (%) |
|---|---|---|---|---|---|
| 24 | [Bmim][InCl$_4$]—1NaI | 79.4 | 39.0 | 12.7/9.4 | 18.3 |
| 25 | [Bmim][InCl$_4$]—2NaI | 75.5 | 39.8 | 16.8/8.3 | 10.6 |
| 26 | [Bmim][InCl$_4$]—3NaI | 86.9 | 44.2 | 12.1/14.6 | 19.9 |
| 27 | [Bmim][InCl$_4$]—4NaI | 79.9 | 44.0 | 15.4/8.7 | 16.8 |
| 2 | [Bmim][InCl$_4$]—5NaI | 85.9 | 47.1 | 26.7/9.9 | 2.1 |

Examples 28-32

Experiment was conducted under the same condition as in Example 2 while varying the amine. The result is shown in Table 6. As seen from Table 6, when various amine compounds were used, amine conversion rate and urea yield were high and the production of reaction byproducts such as AmA was suppressed.

TABLE 6

| Example | Amine | Conversion rate (%) | Urea yield (%) | HPCC yield (%) | AmA yield (%) |
|---|---|---|---|---|---|
| 28 | 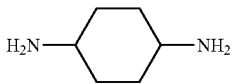 | 80.5 | 50.6 | 33.4 | 6.4 |
| 29 | 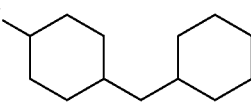 | 90.4 | 66.4 | 20.6 | 3.4 |
| 30 | 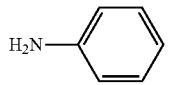 | 50.5 | 33.4 | 18.0 | 6.1 |
| 31 | 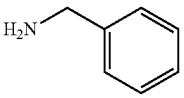 | 80.5 | 49.5 | 20.4 | 2.3 |

TABLE 6-continued

| Example | Amine | Conversion rate (%) | Urea yield (%) | HPCC yield (%) | AmA yield (%) |
|---|---|---|---|---|---|
| 32 | 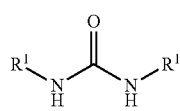 | 48.4 | 20.6 | 20.4 | 4.4 |

While the present disclosure has been described with respect to the specific embodiments, it will be apparent to those skilled in the art that various changes and modifications may be made without departing from the spirit and scope of the disclosure as defined in the following claims.

What is claimed is:

1. A method for preparing a disubstituted urea represented by Chemical Formula 1 and carbamate compounds represented by Chemical Formula 2 and Chemical Formula 3 simultaneously by reacting an amine represented by Chemical Formula 7, carbon dioxide, and an alkylene oxide compound represented by Chemical Formula 8 in the presence of an ionic liquid-based catalyst system containing indium, which is a complex catalyst system represented by Chemical Formula 6 comprising a main catalyst represented by Chemical Formula 4 and an alkali metal halide represented by Chemical Formula 5 as a promoter:

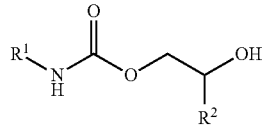 [Chemical Formula 1]

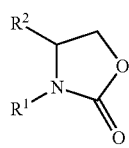 [Chemical Formula 2]

 [Chemical Formula 3]

R$^1$—NH$_2$ [Chemical Formula 7]

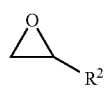 [Chemical Formula 8]

wherein
R$^1$ is a C$_2$-C$_{10}$ aliphatic alkyl group, a C$_4$-C$_{10}$ alicyclic alkyl group or a C$_5$-C$_6$ aryl group, wherein the terminal of the alkyl group or aryl group may be either substituted with a hydroxyl group, an acyl group, a carboxyl group, a halogen atom or an —NH$_2$ group or unsubstituted; and
R$^2$ is a C$_1$-C$_{10}$ aliphatic alkyl group, a C$_4$-C$_{10}$ alicyclic alkyl group, a C$_5$-C$_6$ aryl group, a hydrogen atom, or a halogen atom

[Q][InX$_{(4-n)}$Y$_n$] [Chemical Formula 4]

MZ [Chemical Formula 5]

[Q][InX$_{(4-n)}$Y$_n$]-MZ [Chemical Formula 6]

wherein
[Q] stands for a cation of an ionic [InX$_{(4-n)}$Y$_n$] stands for an anion of the ionic liquid, and MZ stands for an alkali metal halide, wherein Q is imidazolium, phosphonium, ammonium, or pyridinium, X is Cl, Br, or I, Y is Cl or Br, M is an alkali metal, Z is Cl, Br, or I, and n is an integer from 0 to 3.

2. The method of claim 1, wherein the cation of the ionic liquid is selected from the group consisting of 1-butyl-3-methylimidazolium (Bmim), tetra-n-butylphosphonium (TBP), tetra-n-butylammonium (TBA), tetra-n-butylpyridinium (C$_4$Py)$_1$ and choline (Chol); the anion of the ionic liquid is selected from the group consisting of InCl$_4$, InCl$_3$Br, InCl$_3$I, InBr$_3$Cl, and InBr$_4$; and the alkali metal halide is selected from the group consisting of NaI, NaBr, NaCl, KI, KBr, KCl, RbI, RbBr, RbCl, LiI, LiBr, LiCl, CsI, CsBr, and CsCl.

3. The method of claim 1, wherein the main catalyst is used in an amount of 1/5000 equivalent-1/50 equivalent based on the moles of the amine.

4. The method of claim 1, wherein the main catalyst and the promoter are added at an equivalence ratio of 1:1-1:5.

5. The method of claim 1, wherein the alkylene oxide is used in an amount of 0.5 equivalents-2 equivalents based on the moles of the amine.

6. The method of claim 1, wherein the amine is selected from the group consisting of methylamine, ethylamine, isopropylamine, butylamine, isobutylamine, hexylamine, dodecylamine, hexadecylamine, octadecylamine, benzylamine, phenylamine, cyclobutylamine, cyclohexylamine, 1,4-diaminocyclohexane, 4,4'-methylenebis(cyclohexylamine), aniline, benzylamine, and phenylenediamine and the alkylene oxide is selected from the group consisting of ethylene oxide, propylene oxide, butylene oxide, cyclopentene oxide, and cyclohexene oxide.

7. The method of claim 1, comprising performing the reaction for one hour to four hours at 40° C. to 200° C. under a carbon dioxide pressure of 300 psig to 1500 psig.

8. The method of claim 1, comprising performing the reaction either in the absence of a solvent or in the presence of at least one solvent selected from the group consisting of C$_1$-C$_6$ alcohol, tetrahydrofuran (THF), dimethylformamide (DMF), N-methylpyrrolidinone (NMP), dimethyl sulfoxide (DMSO), acetonitrile, toluene, and dioxane.

9. The method of claim 1, wherein the reaction is a one-pot reaction.

* * * * *